US009879305B2

(12) United States Patent
Morales Villagran et al.

(10) Patent No.: US 9,879,305 B2
(45) Date of Patent: Jan. 30, 2018

(54) DEVICE FOR ONLINE MEASUREMENT OF NEUROTRANSMITTERS USING ENZYMATIC REACTORS

(76) Inventors: Alberto Morales Villagran, Zapopan (MX); Daniel Morales Rodriguez, Zapopan (MX)

( * ) Notice: Subject to any disclaimer, the term of this patent is extended or adjusted under 35 U.S.C. 154(b) by 170 days.

(21) Appl. No.: 14/398,426

(22) PCT Filed: May 2, 2012

(86) PCT No.: PCT/MX2012/000045
§ 371 (c)(1),
(2), (4) Date: Feb. 3, 2015

(87) PCT Pub. No.: WO2013/165232
PCT Pub. Date: Nov. 7, 2013

(65) Prior Publication Data
US 2015/0140586 A1    May 21, 2015

(51) Int. Cl.
*C12Q 1/00* (2006.01)
*C12Q 1/52* (2006.01)
*C12Q 1/44* (2006.01)
*G01N 33/94* (2006.01)

(52) U.S. Cl.
CPC ................. *C12Q 1/52* (2013.01); *C12Q 1/44* (2013.01); *G01N 33/9406* (2013.01)

(58) Field of Classification Search
CPC ........ G01N 33/9406; C12Q 1/44; C12Q 1/52; B01L 7/00; B01L 3/52
See application file for complete search history.

(56) References Cited

U.S. PATENT DOCUMENTS

| | | | | |
|---|---|---|---|---|
| 3,770,591 A | * | 11/1973 | Boirat | C12M 41/14 312/236 |
| 5,875,282 A | * | 2/1999 | Jordan | A61M 5/44 165/170 |
| 6,734,398 B1 | * | 5/2004 | Cecchi | B01L 7/00 219/218 |
| 2006/0121624 A1 | * | 6/2006 | Huang | B01L 3/0289 436/180 |

FOREIGN PATENT DOCUMENTS

WO    WO-2010/053342 A1 *  5/2010
WO    WO 2010053342 A1 *  5/2010 ........... G01N 21/645

OTHER PUBLICATIONS

English machine translation of WO 2010053342.*
Derwent English translation of Morales (WO 2010053342) abstract, generated 2017.*

* cited by examiner

*Primary Examiner* — Nathan A Bowers
(74) *Attorney, Agent, or Firm* — Defillo & Associates, Inc.; Evelyn A Defillo (57) ABSTRACT

The invention relates to a device and a method for measuring neurotransmitters in the brain dialysate of mammals using enzymatic reactors specific to a certain neurotransmitter, which generate fluorescent derivatives when mixed. The mixture is introduced into an incubation chamber and passes through a temperature controlling system in order to set it to the optimum enzymatic reaction temperature, and the fluorescent derivative generated is passed through a flow fluorescence cell located inside the incubation chamber, where the liquid is impacted with a laser light source via an optical fiber. The fluorescence emitted is captured by a fluorescence detector that sends it to a processing system in order to obtain the corresponding values.

10 Claims, 5 Drawing Sheets

FIG. 6

DEVICE FOR ONLINE MEASUREMENT OF NEUROTRANSMITTERS USING ENZYMATIC REACTORS

CROSS REFERENCE TO RELATED APPLICATION

This application is a national stage entry of PCT/MX2012/000045 filed May 2, 2012, under the International Convention.

BACKGROUND OF THE INVENTION

Field of the Invention

The present invention relates to a device and method for the measurement of neurotransmitters in the dialysate from a probe implanted in the brain of experimental animals by the use of enzymatic reactants, which are immediately added to the output of the dialysate and using controlled reaction, generate secondary derivatives which can produce fluorescence when impacting with a specific wavelength and whose intensity is proportional to the concentration of the compound of interest

Prior Art

Quantitation of a particular compound in dialysate samples and repetitively, may be related to the use of fraction collectors and auto-samplers that are commonly coupled to another device that may be a liquid chromatography system with high resolution (HPLC) or capillary electrophoresis to name just a few possibilities. In this process, the previous separation of the sample components is most commonly used, so that in the market there are different separation columns and methods for a particular group of compounds such as amino acids, monoamines, carbohydrates, etc. After the separation process, the detection is carried out taking into account the physicochemical properties of these compounds, such as the capacity of oxidation or reduction or absorb light or emit light in the case of fluorescence induction. The diversity of equipment and systems for detecting and analyzing existing thereon is extensive. To use these analytical processes an extensive training is required and also consider care of equipment and all the optimal conditions for adequate preparation of calibration curves before the individual analysis of each of the samples, which can usually take at least 15 minutes Another possibility for quantitative analysis, without the need for prior separation of the compound, is the use of biosensors or enzymatic reactants series of reactions that ultimately lead to a derivative that can be identified by various methods, including: electrochemical and optical principally these latter being the most used. By using auto-samplers and dosing devices an efficient analysis of a large number of samples can be carried out in a short time, so these methods are now very popular and several variants of this approach are now used for the measurement of a large number of compounds.

Invariably, for measuring any compound present in a sample of dialysate a minimum volumen is needed, which depends on the device to be used. In the case of HPLC, the necessary volume can be started from the 5 microliters while for plate readers the needed suitable volume is about 200 microliters.

Each analysis method has its advantages and disadvantages, which the analyst must take into account when selecting the best method and procedure according to the goals pursued; the chromatographic methods being the best positioned, although care and costs, and the time it takes the analysis, can be an important limitation.

Cerebral Microdialysis.

Cerebral microdialysis is the process most commonly used to monitor the concentrations of various neurotransmitters in discrete brain areas, this in order to better understand its function during both normal behavioral and pathological or physiological activity. This technique is used almost exclusively for research purposes and to a very limited extent for clinical purposes. The principle is based on insertion into the brain of a small dialysis probe having an inlet and outlet in which artificial cerebrospinal fluid (CSF) is flowed and the compounds in the extracellular space penetrate into the tube by concentration gradient. The fluid infused through the probe does not penetrate the brain, it is used only as a transport medium of the compounds present in the extracellular space, such that the same amount of fluid is introduced is the same that leaves, but now with identifiable amounts of various biological compounds, among which neurotransmitters such as: glutamic acid, gamma amino butyric acid, acetylcholine and various monoamines. The output fluid is collected analyst is interested. This process is mainly coupled to high-resolution liquid chromatography processes and capillary electrophoresis in which after the separation process the quantitative identification is carried out primarily by means of electrochemical and optical detection systems (mainly fluorescent).

In the market, there are various comercial establishments where the user can select the types and sizes of the probes and the pore of membrane by which the size of the molecules to be retrieved within the probe can be selected. The cut size is between 6,000 and 100,000 Daltons.

Regular dialysate sample collection is mainly taken as a reflection of what happens biochemically in the brain and thus changes in the concentration of various compounds can be related with normal or pathological activity of spatial and temporal form. Dialysate process is carried out generally at a flow rate of 2 microliters per minute so that the temporal resolution by which the biochemical changes can be studied depends on the frequency with which samples are collected. Therefore, the frequency is directly related to the minimum volume required by the methodology of choice, which for HPLC techniques are around the 5-10 minutes for sample collection and in a very few cases one minute.

For processes of capillary electrophoresis, the sample amount is smaller and several studies have been reported with better temporal resolution, including 12 seconds. However, the analysis time is considerable, particularly when a large number of samples is wished to measure wherein in the best analysis time of each simple is at least 10 minutes.

With regard to the measurement of neurotransmitters using enzymatic reactants, some options have emerged on the market, for example, the Swedish company, "CMA Microdialysis", world leader in products and accessories for the microdialysis technique, offers a device that can automatically process up to 30 samples in one hour, with a minimum volume of 2 microliters. Similarly, the patent document WO 2010/053342 A1 describes the measurement of the concentration of certain neurotransmitters by fluorescence measurement at similar sample volumes.

Need for Better Temporal Resolution.

Changes and/or alterations in the concentration of various neurotransmitters in the extracellular space measured by microdialysis technique have been always associated with behavioral and electrophysiological activity, either normal or pathological behavior. However, these events are extremely fast, particularly EEG activity, which may change even in periods of less than one second, so that what is measured in dialysate samples reflect an averaged activity of such activities by the duration of the collection. For this reason, it is required to measure these changes with temporal resolution of one second or less, so that the methodologies and tools available in the market do not resolve this requirement so far. By using electrochemical biosensors embedded in the brain, this paradigm has been tried to solve but the time said means last is limited and unfortunately they are losing activity. Furthermore, to date there is no possibility to build biosensors for the great variety of neurotransmitters in the brain dialysate.

Principles of Measurement of Neurotransmitters by Enzymatic Reactants.

For identification of various substances the enzyme or group of enzymes related to the catalytic process of the compound of interest are commonly used. In the particular case of the present invention, the enzymes related to the catabolism of neurotransmitters are used: glutamate, acetylcholine and GABA in order to generate derivatives that can be measured by fluorescence.

For measurement of glutamic acid the following reaction principles are used: the reactant contains glutamate oxidase and peroxidase enzymes; the firstly mentioned produces H2O2 and a-ketoglutarate, and the second degrades the peroxide generated in the first reaction with the subsequent production of O2 and H2O, said reaction being revealed by the presence of compound AMPLEX RED in the presence of the peroxidase enzyme, which on oxidation produces the resorufin compound, which when impacted with monochromatic light at a wavelength of 561 nm emits fluorescence at 588 nm, whose intensity is proportional to the concentration of this neurotransmitter. The introduction of the enzyme L-glutamate-pyruvate-transaminase and alanine into the ketoglutarate initially occurred, thereby amplifying the signal, by multiple cycles of the initial reaction.

Measurement of acetylcholine in the dialysate is performed similarly, the difference being the use of different enzymes. In this case, the enzymes used are: acetylcholinesterase, choline oxidase and Peroxidase.

Acetylcholinesterase degrades acetylcholine to produce choline and acetate, choline oxidase produces H2O2 and betaine. The generated H2O2 is identified and quantified in a similar manner to the previous experiment, that is, with AMPLEX RED, but in this case the cycling process is not possible.

Quantitative determination of the neurotransmitter GABA is performed by enzymatic reactions coupled by two enzymes: GABA transaminase (GABA-T) and succinate dehydrogenase (SSD) which are termed "Gabasa" as a whole. Enzymatic reactions are:

GABA+acetoglutarate(GABA-T)→L glutamic+succinic semialdehyde succinic semialdehyde+NADP(SSD)→succinic acid+NADPH+H The produced NADPH is capable of emitting fluorescence by the order of 450 nm when excited with ultraviolet light (355 nm). The emission is proportional to the concentration of GABA present in each sample.

OBJECTS OF THE INVENTION

The main objective of the present invention is to propose a new device for measurement of neurotransmitters in the brain dialysate by using enzymatic reactants, with better temporal resolution on the behavioral and electrophysiological events.

Another object of the invention is to propose a method for the measurement of neurotransmitters in the brain dialysate by using enzymatic reactants.

The above object is achieved by a device comprising, in a preferred embodiment of realization, an incubation chamber containing a fluorescence cell connected in fluid flow communication with means for supplying via respective feeding pipes, on the one side, the brain dialysate and, on the other side, an enzymatic reactant specific to a neurotransmitter, which are mixed when they converge in a pipe Y-connector, from which the resulting mixture flows through of a fused silica tube towards the cell fluorescence; and a heating system in said incubation chamber comprising a temperature control element to provide optimum temperature conditions for the enzymatic reaction.

On the other hand, the method of measuring neurotransmitters of the present invention is characterized by the following steps:

selecting and preparing a specific enzymatic reactant of a neurotransmitter of interest;

displacing a predetermined volume of the prepared enzymatic reactant through a first flow supplying pipe by means of a programmable driving device; wherein said first pipe is in flow communication with the Y-connector;

displacing a volume of artificial cerebrospinal fluid through a second flow supplying pipe by means of said programmable driving device; thus, the movement of fluids through their respective pipes is carried out at the same speed;

passing the artificial cerebrospinal fluid through a dialysis probe whose output is connected to an input of a Y-connector located inside an incubation chamber;

flowing together the enzymatic reactant and the brain dialysate through the Y-connector to mix them;

conditioning the incubation chamber at an optimal temperature for the enzymatic reaction and directing the resulting mixture through a fused silica tube into a cell fluorescence to be subjected to a process of excitation and emission of fluorescence;

exciting said mixture in the fluorescence cell with a laser of 561 nm; and capturing the emitted light, after filtering it, with a fluorescence detector at about 588 nm.

The conduction of the excitation and emission light is performed by optical fibers of 600 micron, which are prepared with the appropriate measures for the device designed to carry out this method.

DETAILED DESCRIPTION OF THE PREFERRED EMBODIMENT OF INVENTION

To solve the problem of measuring neurotransmitter with better temporal resolution on the behavioral and electrophysiological events, the present invention is based on the design of a device in which the brain dialysate is collected simultaneously with a specific enzymatic reactant for certain neurotransmitter.

Figure 1:
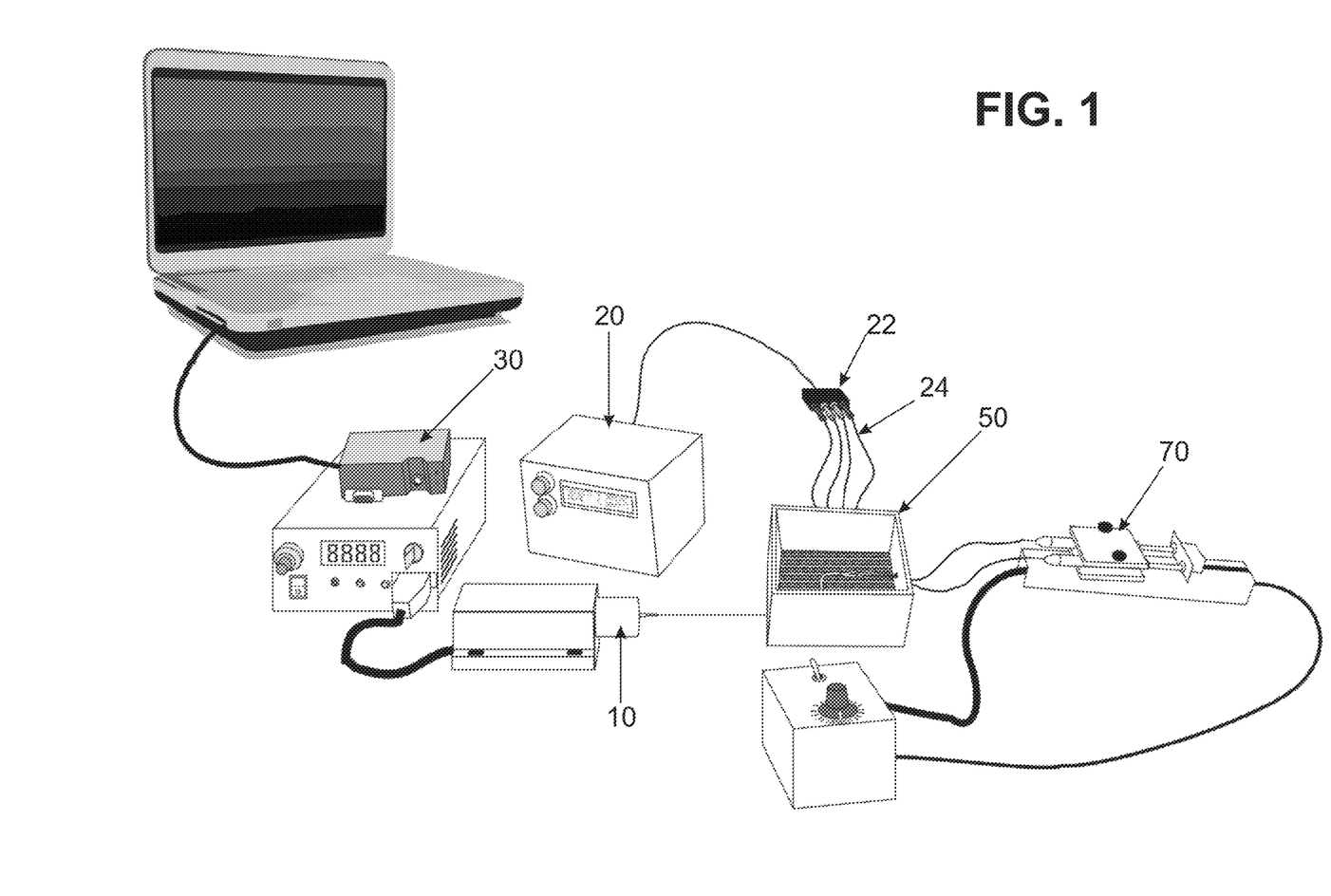
FIG. 1 is a general schematic view of a system for measuring neurotransmitters by using enzymatic reactants.
Figure 2:
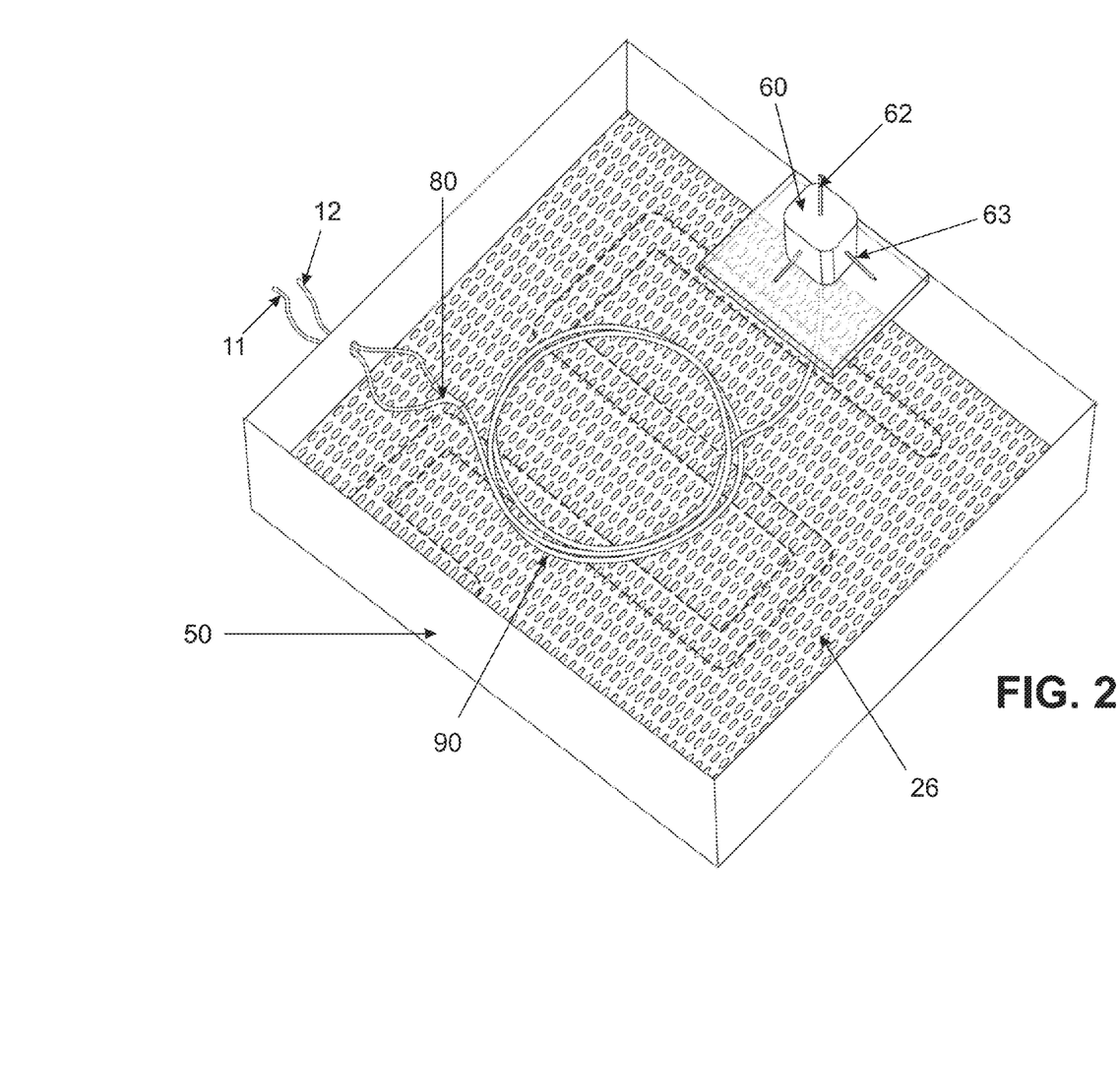
FIG. 2 is a perspective view of the incubation chamber of the measuring device of the present invention.

The device comprises an incubation chamber (50) containing a fluorescence cell (60) connected in fluid flow communication with infusion pumps (70) adapted to supply through respective supplying pipes (120 microns internal diameter), on the one side, a brain dialysate and, on the other side, a enzymatic reactant specific to a neurotransmitter, which are mixed where the supplying pipes converge in a Y-connector (80). In turn, the connector (80) is connected to a fused silica tube (90) of 400 micron outer diameter and 200 micron inner diameter and about 30 em long, through which the resulting mixture flows into the fluorescence cell (60).

The mixture is passed through the fused silica tube (90) placed inside the incubation chamber (50) which is adjusted at the optimal temperature of the enzymatic reaction by using a temperature control element (20). The preselected length of the tube (90) can provide sufficient time for the reaction of the enzymes with the substrate is carried out to generate the fluorescent product which passes through the flow fluorescence cell (60) placed within the incubation chamber (50). The liquid continuously flowing through said cell is impacted with a laser light source (10) (MGL-11-561, Opto Engine LLC) by means of an optical fiber (Polymicro Technologies, Inc.) 600 microns in diameter. Another optical fiber of equal diameter and perpendicular to said cell is disposed to capture the emitted fluorescence, after filtering the unwanted or nonspecific light through a light filter provided for this purpose.

The measurement of fluorescence may be made by a detector (30) CCD (USB 4000) "OceanOptics®" or a photomultiplier, and readings are processed "offline". Through this arrangement, the periodic collection of samples is avoided and the fluorescence intensity is read at various intervals, so that the temporal resolution is determined by the speed at which the reading is taken. Data readings are provided every 200 milliseconds herein below.

Another critical point in the use of enzymatic reactants is the control of temperature, since each enzyme or group of enzymes have an optimum reaction temperature and it is desirable that the incubation of the samples is carried out at the appropriate temperature. Therefore, the device of this invention comprises heating means including a temperature controller (20), which works by means of voltage pulses induced in a microprocessor programmed to achieve a resolution of ±0.1° C., this in the control range from the room temperature to 40° C.

The heating means comprises an oven (22) of adjustable temperature in the optimum range of most enzymes, which includes perforations for connection with ducts (24) for communicating fluid flow and a mat (26) of adjustable temperature for incubation of the mixture of dialysate and enzymatic reactants.

For online measurement of at least three neurotransmitters in the brain dialysate: Glutamic, acetylcholine and GABA, enzymatic reactants specific for each of these compounds are prepared in 100 mM phosphate solution at a pH of 7.0. For the use of each of the reactants is necessary to optimize the conditions of temperature and time of incubation, and the concentration of each of the enzymes and substrates to be used.

For the test method, the conditions and concentrations of enzyme and substrate for measurement of glutamic acid are described in a range of known concentrations of the following components at the indicated final concentration:

Glutamato oxidase 0.16 U/ml
Peroxidase 80 U/ml
L-glutamate-pyruvate-transaminase 0.5 U/ml
Amplex Red 200 µM
L alanine 200 µM Once the enzymatic reactant is prepared, a 1 ml syringe is filled and placed in a programmable driving device (30) which will push the syringe plunger to displace a predetermined volume. Similarly, another syringe is filled with artificial cerebrospinal fluid and is also placed in the driving device, such that the displacement of fluids is performed at the same speed, i.e. 2.5 µ/min, for the examplary case described herein.

The artificial cerebrospinal fluid is passed through one of the inputs of the dialysis probe and the output is connected to one input of Y-connector (80) that is located inside the incubation chamber (50). In the other input of Y-connector a pipe for flowing the enzymatic reactant is coupled, so that it is in the connector (80) where the mixing is carried out, either of the standard solution provided by immersing the probe into known concentration solutions of glutamic acid or from the probe inserted into the brain of experimental animals. The output of the Y-connector is connected to the inlet of the fused silica tube (90) whose output or opposite end is connected to the fluorescence cell (60) having an internal volume of about 1 microliter in the zone of excitation and emission of fluorescence.

Figures 3, 4:
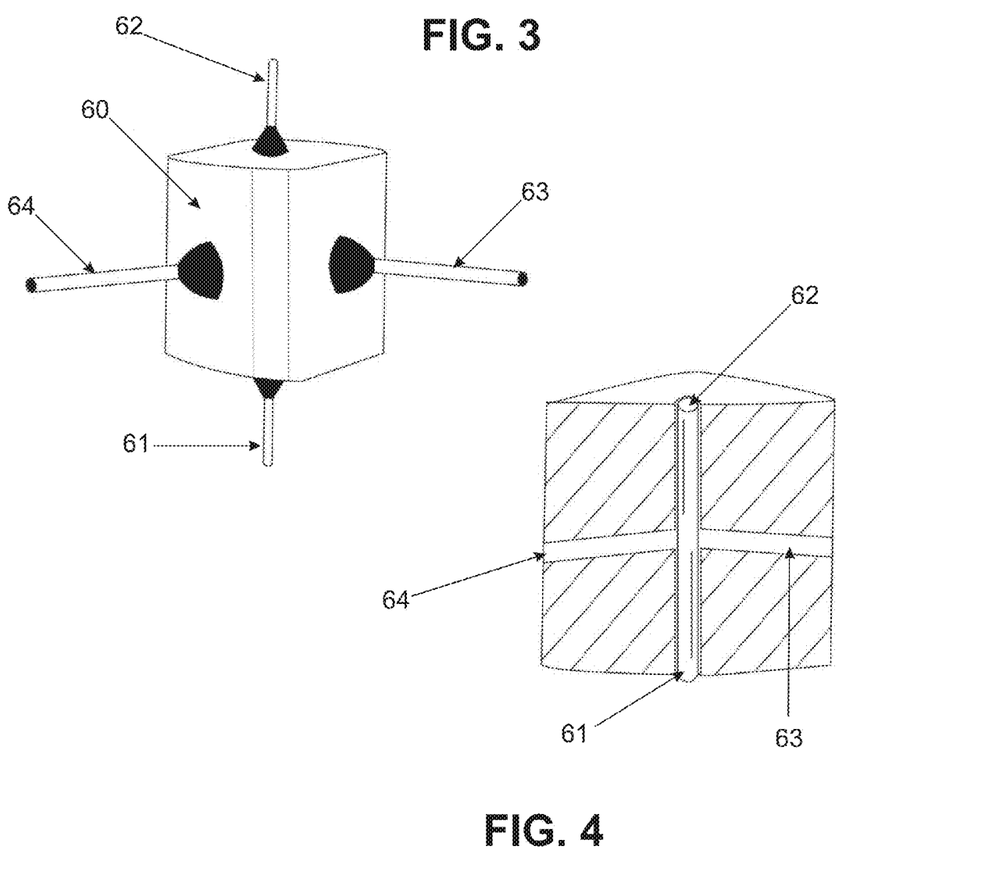
FIG. 3 is a front view of the fluorescence measuring cell.
FIG. 4 is a longitudinal sectional view of the fluorescence cell of the device.

The fluorescence cell (60) comprises a container transparent to light of about 0.8 mm per side and 1.5 mm long (0.96 microliters), to allow the reading of fluorescence in a small volume. Furthermore, said cell comprises an inlet conduit (61) to which the silica tube (90) is connected to allow the mixture to flow into said cell; an outlet conduit (62) for channeling the waste to the outside of the cell after the mixture has been subjected to excitation; a second inlet conduit (63) to which the laser light source (10) is connected via optic fiber for excitation of the sample; and a second outlet conduit (64) perpendicular to the second inlet conduit (63) for directing via optic fiber the emitted fluorescence light produced by excitation of the sample to the fluorescence detector (30) or photomultiplier.

Both the connector (80) as the silica tube (90) and fluorescence cell (60) are located in the incubation chamber (50), which allows the reaction to be carried out always under the same conditions. The excitation of the mixture is performed with the laser (10) of 561 nm and the emitted light is collected—after filtering it—at 588 nm with the fluorescence detector (30), for example, a USB 4000 model of OceanOptics®, or with a photomultiplier. Conduction of light for excitation and emission is performed by optical fibers of 600 microns (Polymicro Technologies), which are prepared with the appropriate measures designed for this device.

All connections are made with pipe used for the microdyalisis process, which has an internal diameter of 0.12 mm. The fused silica tube used in this exemplary method is 200 microns internal diameter and a length of about 30 cm.

Example of Method of Measuring Neurotransmitters.

In an exemplary embodiment, the method of online measurement of neurotransmitters by using enzyme reactant, comprises the following steps:

selecting and preparing a specific enzymatic reactant for a neurotransmitter of interest;

displacing a predetermined volume of the prepared enzymatic reactant through a first flow supplying pipe (11) by means of a driving device (70); wherein said first pipe is in flow communication with a Y-connector (80) located inside an incubation chamber (50);

displacing a volume of artificial cerebrospinal fluid through a second flow supplying pipe (12) by means of said driving device (70); said second pipe being in flow communication with Y-connector; wherein the injection of fluidsthrough the first and second pipes is carried out at the same speed;

passing the artificial cerebrospinal fluid through a dialysis probe whose output is connected to an input of connector "Y";

mixing the enzymatic reactant and the brain dialysate by making them to converge simultaneously in the "Y" connector (80);

passing the mixture of dialysate and the enzymatic reactant through a fused silica tube (90) disposed within the incubation chamber (50) and to a fluorescence cell (60) to subject said mixture to a process of excitation and emission of fluorescence; wherein the silica tube length has been calculated for the mixture to reach the suitable reaction conditions during its travel before entering into the fluorescence cell;

exciting the mixture continuously flowing through the fluorescence cell (60) by impacting it with laser light of 561 nm transmitted via optical fiber by an excitation device (10); and capturing the emitted light by means of optical fiber, after filtering it, with a fluorescence detector at about 588 nm.

Results Obtained with the Device for Online Measurement of Neurotransmitters.

Figure 6:
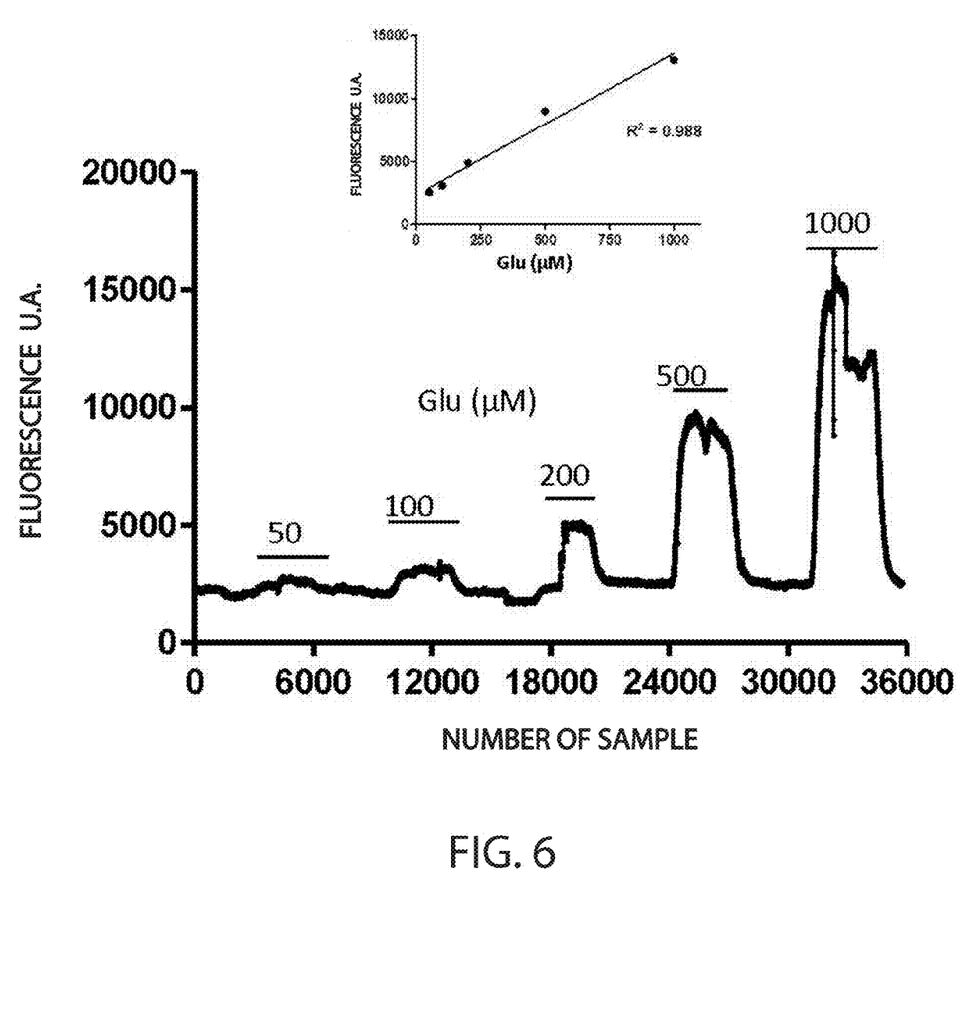
FIG. 6 is a graph of results obtained from implementing the measuring method according to the sample proposed by way of example.

To determine the feasibility of the device, a test of recovery of glutamic acid in dialysate standards at different concentrations was conducted (FIG. 6). Thus, a dialysis probe continuously perfused with artificial cerebrospinal fluid was immersed in test tubes at different concentrations of glutamic acid, at 0.0, 50, 100, 500 and 1000 µM, for periods of 10 minutes and intervals of 15 minutes at concentrations of 0.0 µM, to allow the recovery of the compound and the return to baseline (zero glutamic acid concentration in the dialysate).

The fluorescence resulting from the reaction with glutamic acid and the specific reactant was taken in the fluorescence cell at intervals of 211 milliseconds, such that the total sampling time was 126 minutes with a total number of 35783 samples. The linear regression analysis shows a coefficient of 0.988 in the tested concentration ranges, which demonstrates that the device is capable of analyzing online fluorescent derivatives with a resolution less than one second.

The graph in FIG. 6 is representative of the test carried out for measuring online glutamic acid at different concentrations 100, 200, 500 and 1000 micromolar. The probe was immersed in each of the above concentrations for 10 minutes and returned to a glutamic-free tube, which allows to see as the fluorescence increases in proportion to the concentration. The total population of samples is 35,783.

Figure 5:
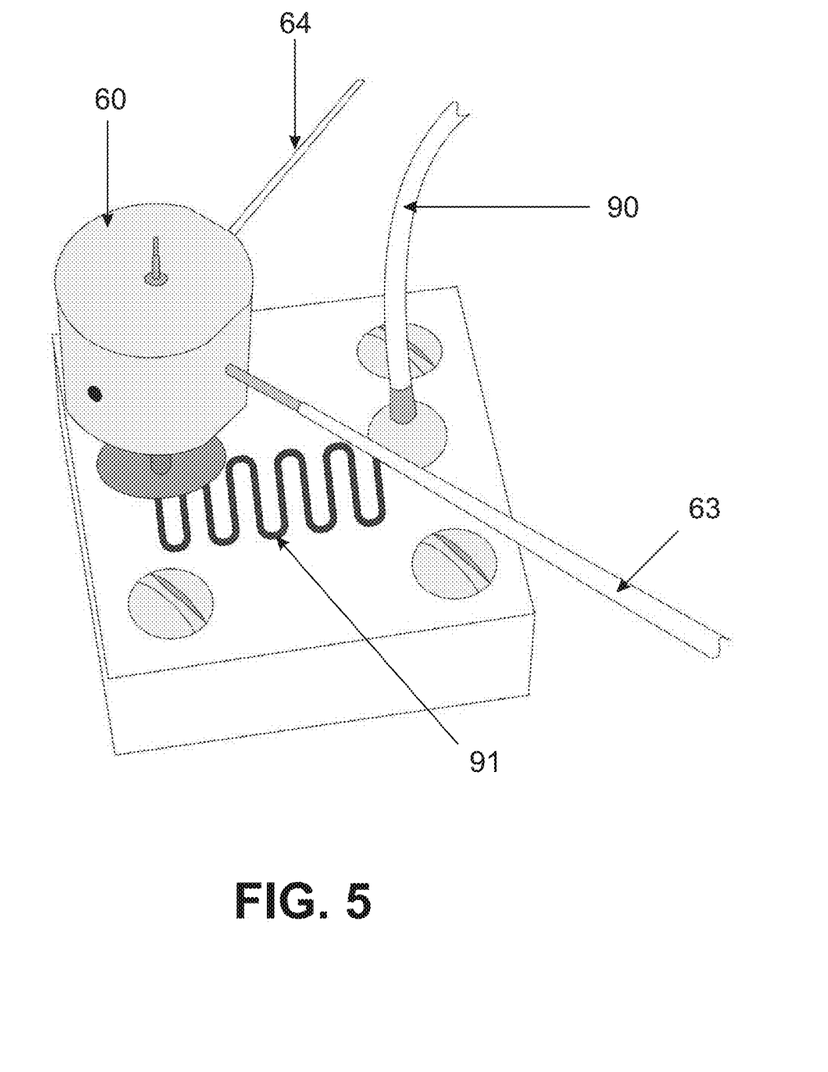
FIG. 5 is an enlarged view of the area where the fluorescence cell is installed, in an alternate embodiment mode.

Finally, FIG. 5 illustrates a variant of the supply line of the mixture of brain dialysate and enzymatic reactant, wherein a coil (91) connected to the silica tube (90) is disposed before the sample enters into the fluorescence cell (60).

Although the invention has been described in the context of the mode or preferred embodiment, it will be evident to those skilled in the art that the scope of the exemplified concept extends beyond the design of the device and method specifically described and illustrated to other embodiments of the invention that are feasible or viable. Moreover, while the invention has been described in detail, a skilled person in the art to which the invention belongs can deduce that some elements/steps of the device or method can be substituted or others added in the light of the above description without modifying essentially the result for which they are intended.

Given the foregoing, it is intended that the scope of the present invention is not interpreted as limited by the particular embodiment described, but rather is determined by a reasonable interpretation of the content of the following claims.

What is claimed is:

1. A device for online measurement of neurotransmitters comprising:
   an incubation chamber made of a light transparent material, the incubation chamber including inside:
      a fluorescent cell having a first inlet, a second inlet, a first outlet, and a second outlet, wherein the second outlet conduit is perpendicular to the second inlet conduit;
      a silica tube having a first end connected to the first inlet of the fluorescent cell;
      a Y-connector connected to a second end of the silica tube, the Y-connector having a first end and a second end; and
      an adjustable temperature mat located on a bottom of the incubation chamber;
   a pump having a first pipe in fluid flow communication with the pump adapted to transport a brain dialysate to the first end of the Y-connector inside the incubation chamber and a second pipe in fluid flow communication with the pump adapted to transport a selected enzymatic reactant to the second end of the Y-connector inside the incubation chamber, wherein the brain dialysate and the selected enzymatic reactant converge simultaneously in the Y-connector forming a mixture;
   a laser light source connected to the second inlet of the fluorescent cell by using an optical fiber, the laser light source emits a laser light for excitation of the mixture flowing through the fluorescent cell;
   a heating device connected to the mat to regulate the temperature of the mat;
   a fluorescence detecting and measuring device connected to the second outlet of the fluorescent cell through optical fiber for detection and measurement of fluorescent light emitted by the mixture subjected to excitation; and
   wherein when the mixture passes through the silica tube placed inside the incubation chamber, the mat heats the mixture to an optimal temperature for the enzymatic reactant.

2. The device of claim 1, wherein the silica tube is made of a fused silica tube.

3. The device of claim 1, wherein the incubation chamber is about 0.8 mm per side and 1.5 mm long (0.96 microliters).

4. The device of claim 1, wherein the optical fibers have a diameter of 600 microns.

5. The device of claim 1, wherein the heating device comprises a temperature control by induction of voltage pulses programmed in a microprocessor to achieve a resolution of ±O.PC.

6. The device of claim 1, wherein the heating device further comprises a temperature controlled oven including perforations for connection to the mat.

7. The device of claim 1, wherein the fluorescence detecting and measuring device is a CCD detector and/or a photomultiplier.

8. The device of claim 1, wherein the first pipe and the second pipe of the pump have a capillary of 0.8 mm square and 1.5 mm straight section.

9. The device of claim 1, wherein the device analyzes online fluorescent derivatives with a resolution less than one second.

10. The device of claim 1, wherein the fluorescent cell has an internal volume of about 1 microliter at the area of fluorescence excitation and emission.

* * * * *